United States Patent
Luce

(10) Patent No.: US 10,258,495 B2
(45) Date of Patent: Apr. 16, 2019

(54) OSTOMY APPLIANCE GUARD

(76) Inventor: Donna E. Luce, Duncanville, TX (US)

( * ) Notice: Subject to any disclaimer, the term of this patent is extended or adjusted under 35 U.S.C. 154(b) by 362 days.

(21) Appl. No.: 14/131,270

(22) PCT Filed: Jul. 11, 2012

(86) PCT No.: PCT/US2012/046221
§ 371 (c)(1),
(2), (4) Date: Jan. 7, 2014

(87) PCT Pub. No.: WO2013/009848
PCT Pub. Date: Jan. 17, 2013

(65) Prior Publication Data
US 2014/0148771 A1    May 29, 2014

Related U.S. Application Data

(60) Provisional application No. 61/506,484, filed on Jul. 11, 2011.

(51) Int. Cl.
| | | |
|---|---|---|
| A61F 5/448 | (2006.01) | |
| A61F 5/449 | (2006.01) | |
| A61F 5/445 | (2006.01) | |

(52) U.S. Cl.
CPC ............. *A61F 5/448* (2013.01); *A61F 5/445* (2013.01); *A61F 5/449* (2013.01)

(58) Field of Classification Search
CPC combination set(s) only.
See application file for complete search history.

(56) References Cited

U.S. PATENT DOCUMENTS

| | | | | |
|---|---|---|---|---|
| 1,922,763 A | * | 8/1933 | Gricks | A61F 5/445 604/340 |
| 2,129,054 A | | 9/1938 | Geisler | |
| 2,496,175 A | * | 1/1950 | Perry | A61F 5/445 604/335 |
| 2,549,649 A | * | 4/1951 | Van Hove | A61F 5/445 604/341 |
| 2,656,838 A | * | 10/1953 | McConnell | A61F 5/445 604/340 |

(Continued)

FOREIGN PATENT DOCUMENTS

WO        9716141        5/1997

*Primary Examiner* — Tatyana Zalukaeva
*Assistant Examiner* — Guy K Townsend
(74) *Attorney, Agent, or Firm* — SMU Law School Patent Clinic

(57) ABSTRACT

An guard system that aids ostomy pouching systems in preventing the leakage of waste material, guards the user's stoma from blunt force trauma, aids in stabilizing the peristomal region, and helps the user's stoma to protrude is disclosed. The guard system comprises a substantially rigid body having an annular base ring and a cupped area extending generally outwardly from the annular base ring. The cupped area has a top portion and a bottom portion, and the bottom portion and the annular base ring together define an opening dimensioned to permit a waste collection bag employed by the user to be inserted therethrough during use. The guard further may comprise a connecting means to attach to a belt. The guard system may further comprise an adapter that allows the guard to be used in conjunction with a variety of faceplate flange sizes of user's ostomy appliance and provides other beneficial functions.

20 Claims, 16 Drawing Sheets

(56) References Cited

U.S. PATENT DOCUMENTS

| | | | |
|---|---|---|---|
| 2,675,002 A * | 4/1954 | Cesare | A61F 5/445 604/338 |
| 2,837,094 A | 6/1958 | Cowles | |
| 3,074,404 A * | 1/1963 | Robinson | A61F 5/448 604/338 |
| 3,398,744 A * | 8/1968 | Hooper | A61F 5/445 604/340 |
| 3,773,048 A * | 11/1973 | Kirkliauskas | A61F 5/445 604/345 |
| 4,596,566 A * | 6/1986 | Kay | A61F 5/445 604/176 |
| 4,636,206 A * | 1/1987 | Ederati | A61F 5/4404 604/340 |
| 4,723,952 A | 2/1988 | Esposito | |
| 4,738,257 A | 4/1988 | Meyer | |
| 4,867,749 A | 9/1989 | Steer | |
| 5,125,917 A | 6/1992 | Whealin | |
| 5,178,614 A * | 1/1993 | McDowell | A61F 5/445 604/332 |
| 5,209,744 A * | 5/1993 | Abe | A61F 5/445 604/332 |
| 5,338,315 A | 8/1994 | Baker | |
| 5,653,701 A | 8/1997 | Millman | |
| 5,811,116 A | 9/1998 | Gilman | |
| 6,129,715 A * | 10/2000 | Cunningham | A61F 5/445 128/885 |
| 8,316,985 B2 | 11/2012 | Bain et al. | |
| 8,377,020 B1 * | 2/2013 | Berven | A61F 5/445 604/264 |
| 9,084,696 B2 * | 7/2015 | Luce | A61F 5/44 |
| 2007/0135783 A1 * | 6/2007 | Scott | A61F 5/445 604/337 |
| 2009/0182191 A1 * | 7/2009 | Redlich | A61F 5/445 600/32 |
| 2010/0142858 A1 * | 6/2010 | Kruse | B65D 31/10 383/5 |
| 2010/0191202 A1 | 7/2010 | Hogard et al. | |
| 2010/0241093 A1 | 9/2010 | Hooper | |
| 2012/0283679 A1 * | 11/2012 | Berish | A61F 5/449 604/345 |
| 2014/0148771 A1 * | 5/2014 | Luce | A61F 5/445 604/345 |
| 2015/0088081 A1 * | 3/2015 | Hakel | A61F 5/445 604/337 |

\* cited by examiner

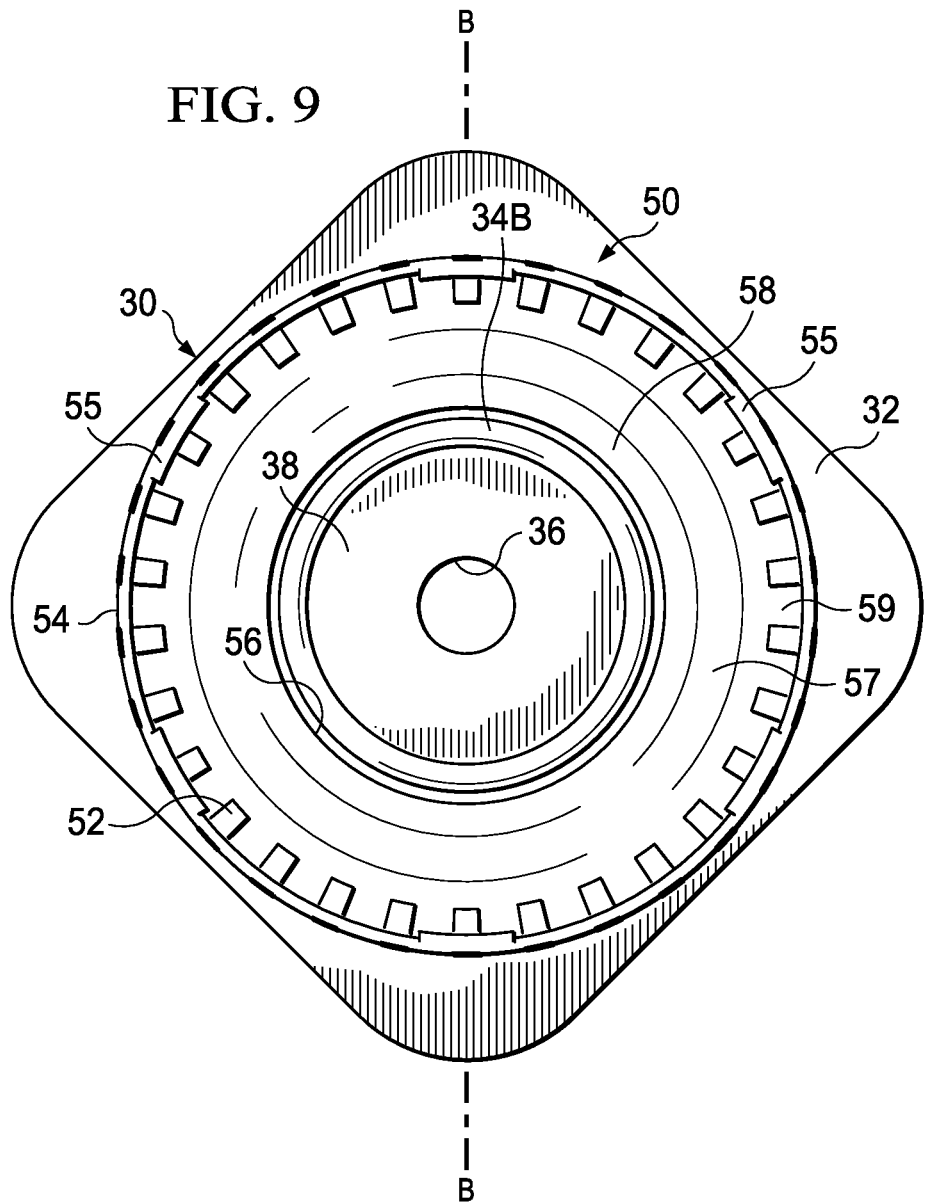

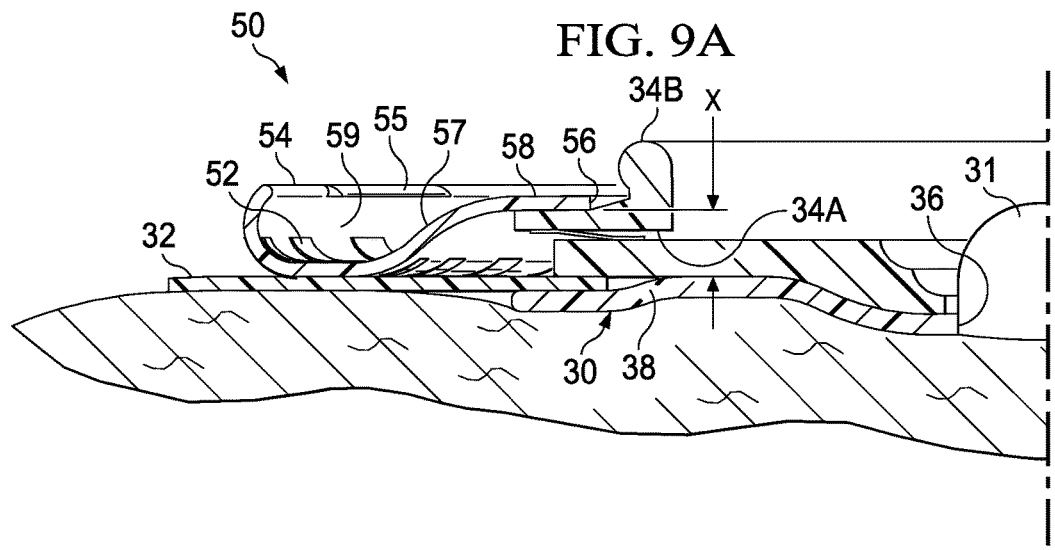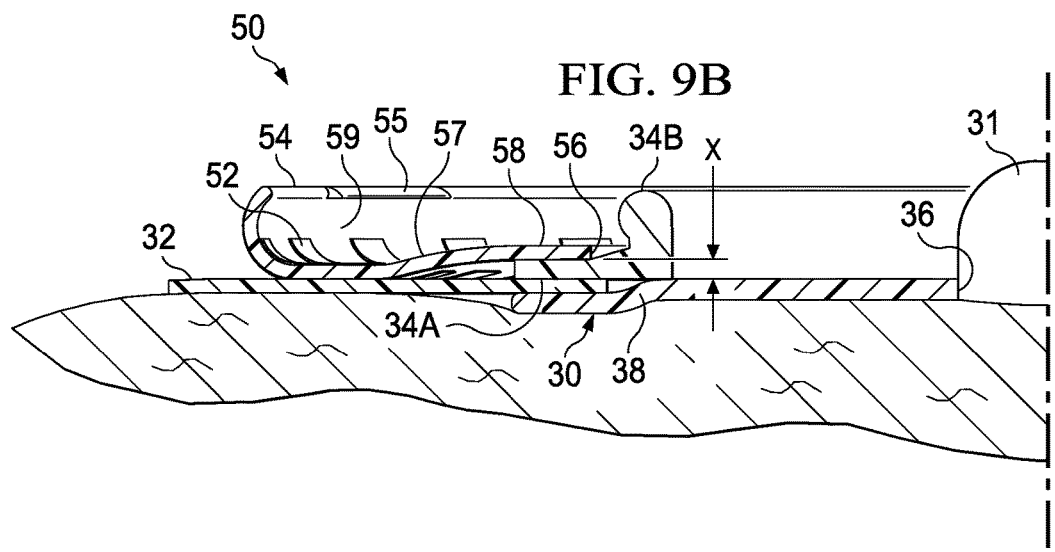

OSTOMY APPLIANCE GUARD

CROSS REFERENCE TO RELATED APPLICATIONS

This application claims the benefit of U.S. Provisional Application No. 61/506,484, filed Jul. 11, 2011.

STATEMENT REGARDING FEDERALLY SPONSORED RESEARCH OR DEVELOPMENT

Not applicable.

TECHNICAL FIELD

The present application relates generally to systems for securing ostomy waste collection pouches to the body and preventing leakage of primary securement means.

BACKGROUND OF THE INVENTION

Ileostomies, colostomies, and similar procedures are surgically created openings in which a portion of the intestine is brought through the abdominal wall to form a stoma, which may be temporary or permanent depending on the reason for surgery, i.e., disease, injury, birth defects or cancer. A pouching system is used to collect waste material. There are two main types of systems commercially available: one-piece pouches with a built-in skin barrier, and two-piece systems composed of a skin barrier and detachable pouch. Skin barriers (or faceplates) are comprised of an adhesive layer formed of a soft skin-friendly hydrocolloid containing adhesive material and provide therein a centrally located aperture to receive a stoma. Systems may further provide a peel and stick tape on the outer edges of a faceplate for additional adhesion. Sticky skin wipes also help with adhesion of tape and the appliance faceplate. These faceplates are attached to the peristomal region of the user to protect the skin from irritating digestive juices. The two-part system provides a flange in the form of a pair of annular or ring-like rigid plastic parts designed to aid in either securing the pouch to the faceplate or removing the pouch at the user's discretion. Pouch styles and sizes vary from manufacturer to manufacturer and may or may not be equipped with a drainable end and may or may not have a filter. A convex faceplate is generally used when a stoma protrudes less than an inch and a flat faceplate is generally used when a stoma protrudes more than an inch.

Ostomates are faced with many problems associated with stomas and stoma waste collection pouches. One critical problem is loss of adhesion of the faceplate from an ostomate's skin, threatening a resulting loss of containment of waste. A faceplate cannot be checked for properly secured adhesion once it is applied to the skin. Loss of adhesion is common and unpredictable, even when directions for use are strictly followed. Subsequent leakage of waste can and does occur, often without warning, soiling clothes, causing unpleasant odors and embarrassment to the wearer. The wearer must immediately cease all activity and promptly address the situation, as flow of waste is continuous and involuntary. Although sticky skin preparations and adhesives are essential, they are not fail-proof due to uncontrollable factors influencing how long a pouching system will stay sealed. Among these factors are: changes in weight, perspiration, skin oils, watery discharge from foods, scars, and strenuous activities, such as sports or work. Fear of public humiliation due to such failures with the pouching adhesion causes many ostomates to avoid returning to normal lifestyle activities, including work and usual attire. There remains a need for a "second line of defense" or more aptly described—a fully engaged physical boundary for when these factors contribute to loss of adhesion.

Another dilemma faced by ostomates is ballooning of the pouch due to intestinal gas. This is especially true with filter-less pouches and presents difficulties over the six to eight hours the wearer is asleep.

Yet another problem faced by ostomates is the inability to return to wearing form-fitted jeans, trousers or other fitted clothing. In many cases, surgical placement of a stoma is often located near one's waistline and as a result, some part of a wearer's faceplate lies directly under a waistband. Current ostomy literature advises that one may return to one's normal mode of dress with a few exceptions. However, wearers often experience a feeling of irritation caused by constricted flow due to wearing form-fitted clothing, and this constriction contributes to loss of adhesion. There remains a need for a device to provide unrestricted flow of output while allowing current ostomy products to function as intended, and to provide a secure boundary against leakage while giving an ostomate the ability to wear form-fitted clothing.

BRIEF DESCRIPTION OF THE DRAWINGS

FIG. 9 is a front view of the adapter of FIG. 8 on a faceplate.

FIG. 9A is a cross sectional view of the adapter of FIG. 8 illustrating one configuration of an integral support wall.

FIG. 9B is a cross sectional view of the adapter of FIG. 8 illustrating another configuration of an integral support wall.

DETAILED DESCRIPTION

Figure 1:
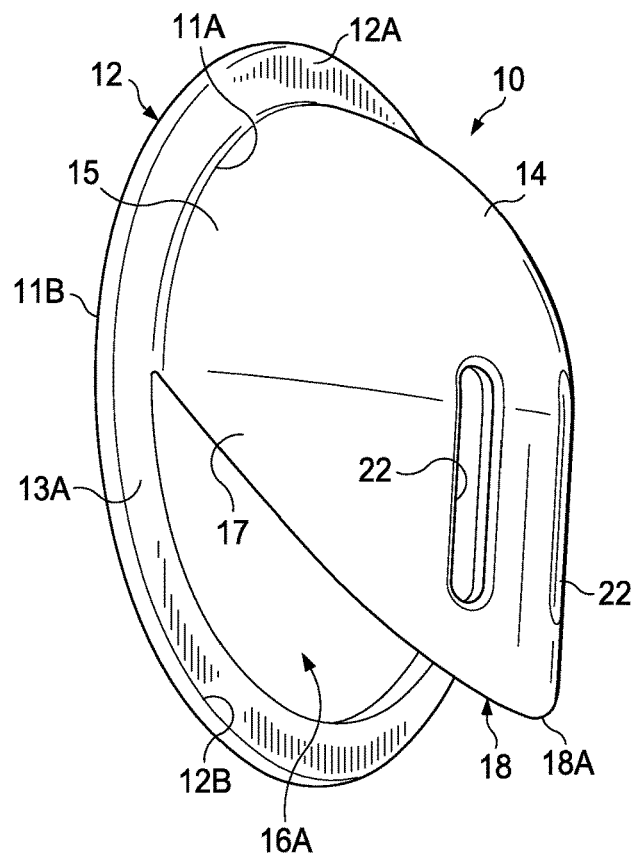
FIG. 1 is a front perspective view of an embodiment of an ostomy guard.

Herein disclosed is a second line of defense or more aptly described—a fully engaged physical boundary that counteracts the effect of factors that can lead to an ostomy appliance not being secured to the body. The invention allows for unrestricted flow of output from the user, allowing current ostomy products to function as intended, and provides a secure boundary against leakage (i.e., loss of containment of bodily waste) by preventing disengagement of the appliance from the body. The device also gives the ostomate the ability to wear form-fitted clothing.

The complementary system for ostomy appliances provides an additional level of security to an ostomate already utilizing a two-piece or one-piece ostomy appliance of the type which is secured to the body with a faceplate comprising an adhesive securement means such as a hydrocolloid adhesive member or a combination of hydrocolloid adhesive member and an integral or non-integral adhesive non-woven fabric or adhesive tape (outer tape portion). The system comprises a generally domed guard for the protection of a stoma and to facilitate comfort in regard to flow of output. In use, the guard lies adjacent the hydrocolloid adhesive member.

The system also may comprise an adapter for the purpose of maintaining the guard's position proximate a stoma and allows one to snap on or remove the subject guard at the user's discretion and further to accommodate various flange sizes commercially available, among other advantages. The adapter is placed so as to encircle the flange on a faceplate of a two-piece ostomy appliance. In the case of a one-piece ostomy appliance, the adapter is placed generally adjacent the connection of the pouch to the faceplate (usually a heat weld) and lying on the faceplate.

The adapter may be worn temporarily without the guard to provide support to the faceplate when the user wears form-fitting clothing.

Prior to proceeding with a more detailed description of the subject invention, it is noted that for the sake of clarity, identical components, which have identical functions, have been identified with identical reference numerals throughout the several views of the attached drawings.

Figure 2:
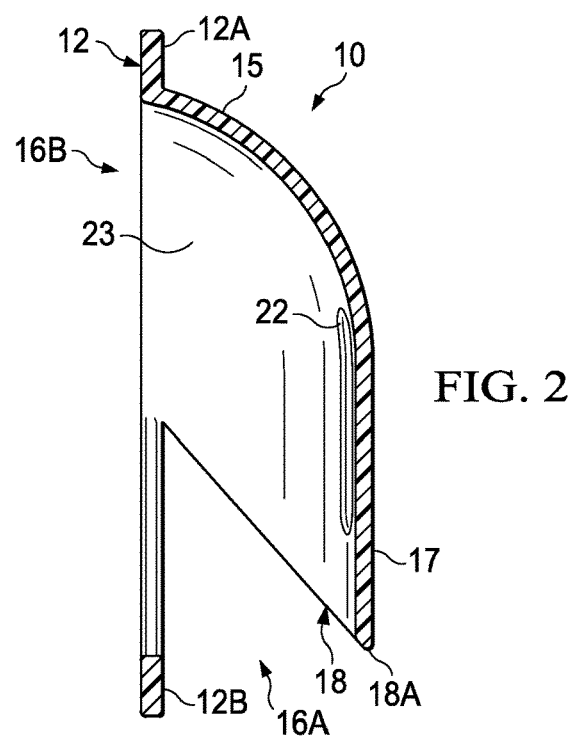
FIG. 2 is a cross-section of the ostomy guard of FIG. 1 along A-A of FIG. 3.
Figure 3:
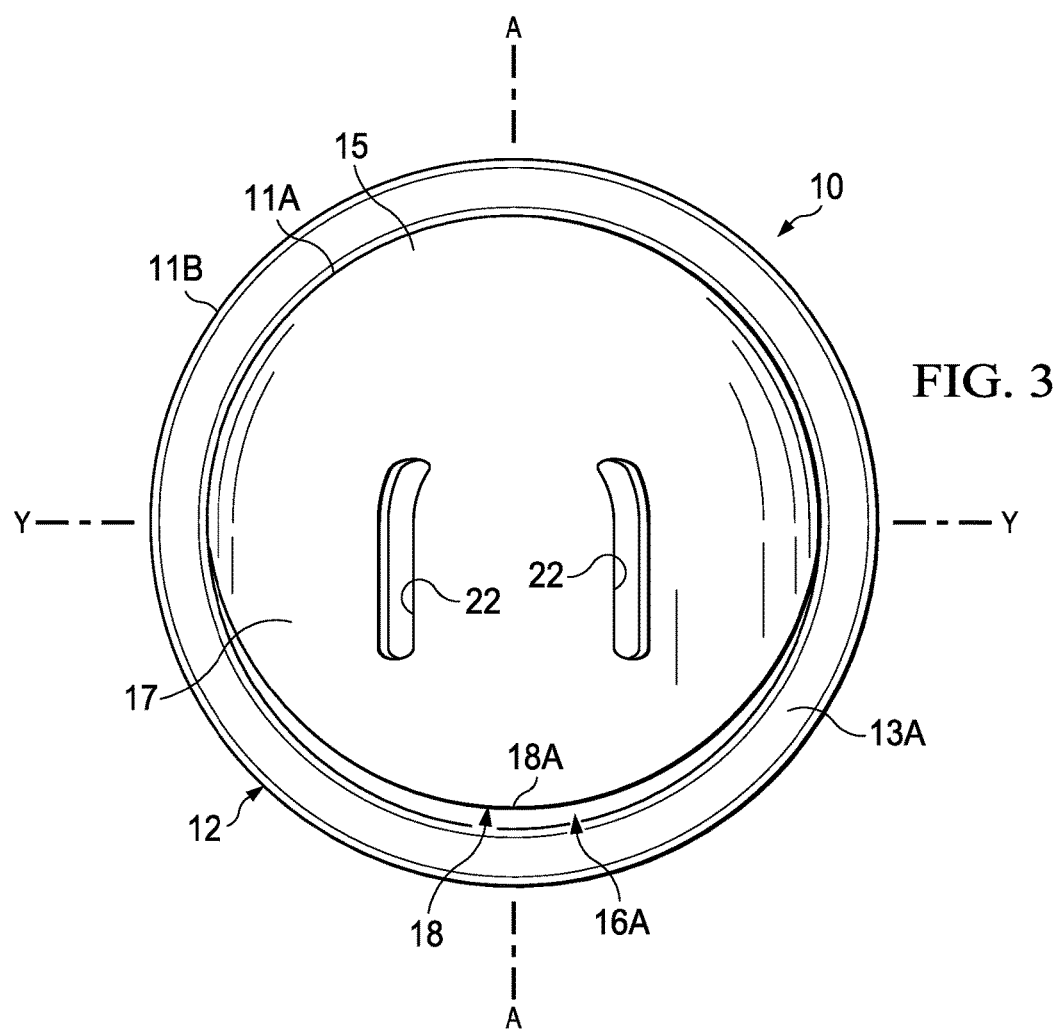
FIG. 3 is a front view of the ostomy guard of FIG. 1.

FIGS. 1-7, 10 and 11, illustrate an embodiment of a guard 10 comprising a cup-shaped body 14 having a top portion 15, generally in the form of a dome in this embodiment, and a bottom portion 17, generally in the form of a cylinder and ending in a parabolic edge 18. Guard 10 further comprises an annular base ring 12 having a first portion 12A and a second portion 12B and an inner circumference 11A and an outer circumference 11B. First portion 12A defines where top portion of body 15 extends outwardly from along inner circumference 11A. Inner circumference 11A of second portion 12B and parabolic edge 18 define a front aperture 16A. Rear central aperture 16B is defined by the entirety of inner circumference 11A, as best seen in FIGS. 2 and 3.

FIG. 2 is a cross section of the embodiment shown in FIGS. 1 and 3 along line A-A of FIG. 3. One can see that bottom portion of body 17 is generally parallel to the annular base ring 12. This provides a more vertical platform for a belt or clothing to press against and thereby evenly distribute pressure or force to underlying annular base ring 12 to provide a second line of defense or seal. Slits 22 may accept a belt that inserts into one slit and out the other, and then fastens around the user's body along the Y-Y axis as labeled in FIG. 3. Any belt fastening means may be used instead of slits. For example, the outer surface of body 14 may be provided with positioning ribs, a hook and loop fastener complementary to a belt fastener, a belt-retaining depression, and/or a combination thereof.

FIG. 2 also best illustrates the cupped area interior of body 14 having an outer surface and an inner (generally concave) surface 23. Body 14 may further comprise additional reinforcements, as may be known in the art, such as polymer reinforcement for various hard plastics or a grid of reinforcing ribs on either the outer or the inner surface, but may be preferred on the inner (concave) surface 23 of the device so that the outer surface remains smooth. The reinforcement can be in any desired arrangement for maximum reinforcing effect. This reinforcement may be desirable not only for protection from outward blunt force trauma to a stoma but additionally to impart the device with resistance to fracture where force is applied from a belt or form fitted clothing.

FIG. 2 also illustrates that the interior of the device provides a cavity to accommodate the stoma and ostomy appliance of the user, and to allow unrestricted flow of output from the stoma.

FIG. 3 is a front view of the embodiment shown in FIGS. 1 and 2. Parabolic edge 18 has vertex 18A. In this illustration, parabolic edge 18 angles back to a point just below the center axis Y-Y, however, variations are contemplated and parabolic edge 18 may angle back to a point further below axis Y-Y (See FIG. 12). This may provide additional strength support within the guard and may help decrease any torque placed on the parabolic edge and annular base ring when using certain materials. Optional belt slits 22 are illustrated. Instead of belt slits 22, alternate belt attachment means as discussed above can be employed in this same vicinity. Guard 10 is generally symmetrical across the A-A axis.

The generally domed shaped top 15 allows one the freedom to bend forward comfortably, although other shapes may be contemplated.

Annular base ring 12 is of sufficient thickness to provide strength, rigidity and resistance to cracking. It has been found that a thickness of at least about 3/16 inches (0.5 cm) is sufficient for most materials. Alternately, a reinforcing ring could be embedded into annular base ring 12 for additional strength.

In this embodiment, annular base ring 12 is generally flat and has sufficient width to avoid discomfort to the wearer. In most cases, the sufficient width will be at least ¼ inch (0.6 cm). Annular base ring 12 may also comprise an edging, such as a soft, rubber like material, that bands or overlays annular base ring 12. Another alternative is applying an attachment means to said annular base ring to facilitate gripping of annular base ring 12 to a surface on the ostomy faceplate. For example a hook or loop material may attach to non-woven tape.

Alternatively, annular base ring 12 can be shaped to be complementary with an optional adapter structure used as part of the system of the invention, which will be discussed in more detail below.

The guard may be formed of any suitable material of sufficient rigidity and durability to absorb and divert external impact forces. Examples of suitable materials include various hard plastics, polypropylene (PP), high density polyethylene (HDPE), acrylonitrile butadiene styrene (ABS), PC/ABS (polycarbonate/ABS blend), polybutylene terephthalate (PBT), metals, polymers, fiber-reinforced polymers, non-toxic metal (e.g., stainless steel) or other like materials and combinations thereof that may be extruded, vacuum or injection molded, stamped, cast, or formed by any suitable process. Holes for ventilation purposes may be added to the guard. Additionally, padding (i.e., foam, rubber, thermoplastic elastomers (TPE), thermoplastic vulcanizates (TPV), and combinations thereof) may be used on any or all hard edges for additional comfort to the wearer and may also be molded over the entire exterior surface. The exterior surface of the guard may also be texturized to aid in positioning of the guard when worn under clothing without a security strap. The guard and adapters may be adjusted in size or dimensions to accommodate, children's sizes, daytime or nighttime wear, and may be in a variety of colors or shapes. It may be beneficial to have a larger nighttime-sized guard to accommodate the buildup of intestinal gas over the six to eight hours the wearer is asleep, while maintaining comfort to the wearer.

Figure 4:
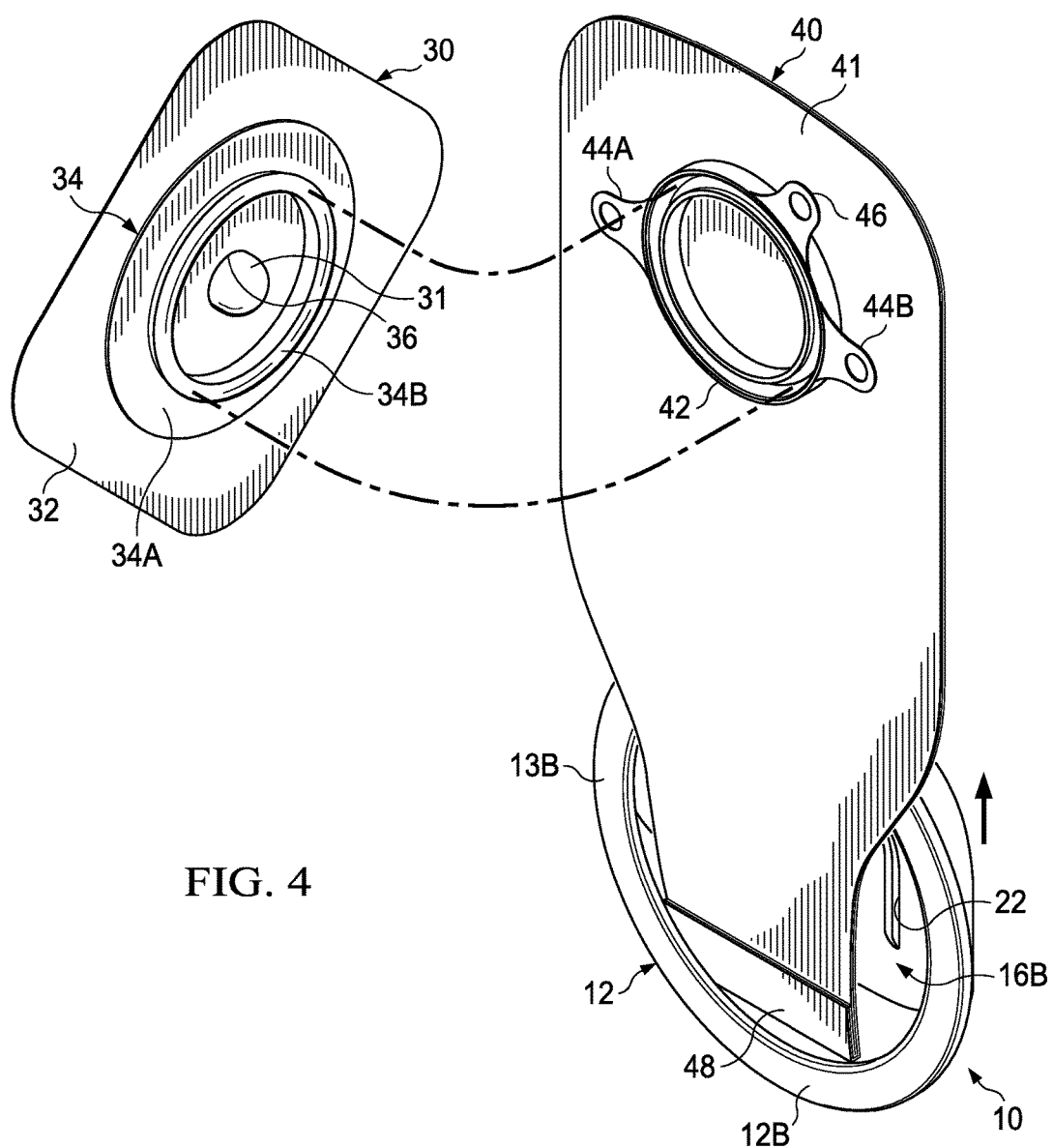
FIG. 4 is a rear perspective view illustrating how to apply and adjust the ostomy guard of FIG. 1.

FIG. 4 illustrates a typical example of a current, commercially available two-piece ostomy pouching system wherein a faceplate 30 is designed to be adhesively attached to the area of skin immediately surrounding a stoma 31 (referred to as the peristomal region) and said faceplate 30 comprises an underlying hydrocolloid adhesive member 38 (best shown in FIGS. 9A and 9B) and an outer tape portion 32 for added bonding. It should be noted that other faceplate and pouch designs are commercially available and may be used with the system of the invention, even though they differ from the typical pouching system illustrated in FIG. 4. Faceplate 30 defines a centrally located stoma aperture 36 to receive the user's stoma 31, and comprises a faceplate flange 34, which comprises coupling member 34B and flange base 34A. FIG. 4 further illustrates that pouch 40 is intended to be attachable and detachable from the faceplate flange coupling member 34B by means of a pouch flange 42 which is adapted to secure to faceplate coupling member. Commercial tabs 44A and 44B on either side of said pouch flange are a means to attach an optional belt, and tab 46 on the upper edge of said flange facilitates easy removal of the pouch 40. A fold and lock drain may be provided at pouch end 48 for emptying waste. The description of a typical pouching system is given simply to indicate how the guard is used by a wearer and is not part of the system of the invention.

The description of a typical pouching system is given simply to indicate how the guard is used by a wearer and is not part of the system of the invention.

Once a pouching system has been installed on a user, the instant invention is applied by guiding pouch end 48 in through rear central aperture 16B of guard 10, then out through front aperture 16A. The arrow in FIG. 4 indicates that guard 10 is then lifted upwards until body 14 of guard 10 encompasses the now engaged flanges, i.e., coupling member 34B and pouch flange 42; and annular base ring 12, which has a front side 13A and a back side 13B, is installed with back side 13B preferably resting upon outer tape portion 32 and may or may not rest on hydrocolloid adhesive member 38 depending on the style of faceplate employed by the user.

Figure 5:
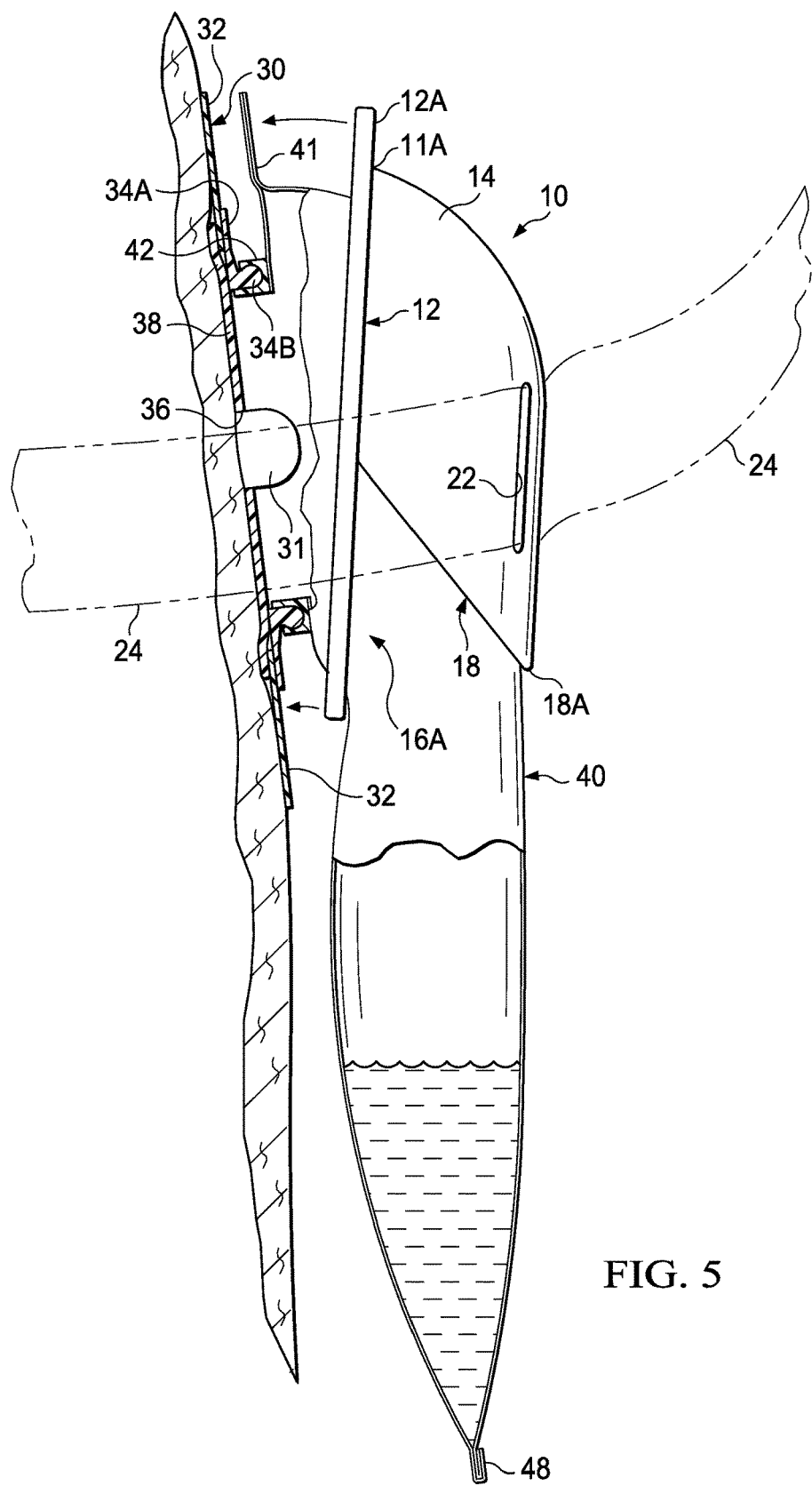
FIG. 5 is an environmental side view of the ostomy guard of FIG. 1 showing near final placement of said device upon a pouching system.
Figure 6:
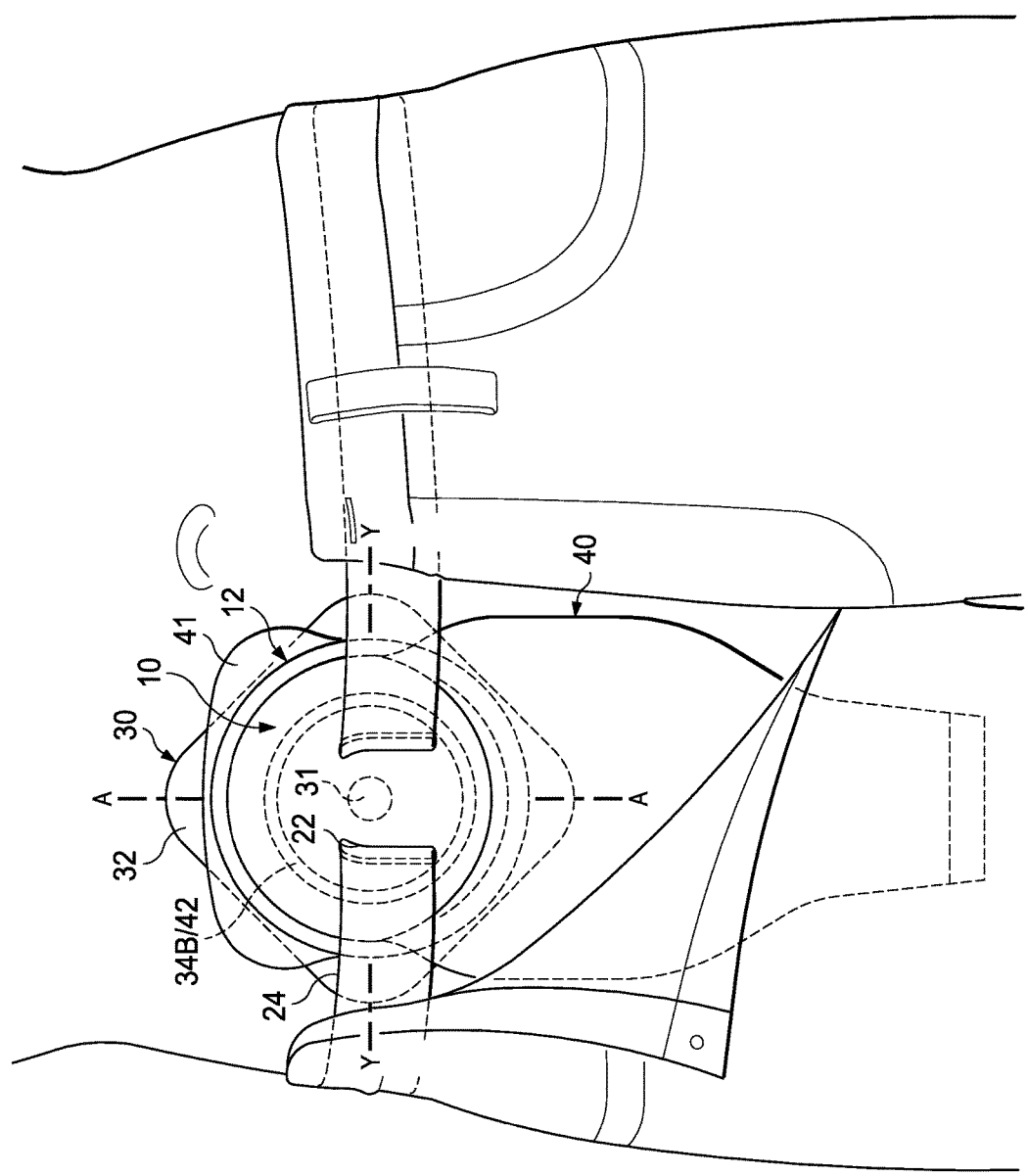
FIG. 6 is an environmental front view of the ostomy guard of FIG. 1 showing its intended position when worn on the torso of a human.

Now referring to FIG. 5, guard 10 is shown as having been moved toward the upper pouch and is nearly in proper position. The arrows shown indicate that annular base ring 12 will fit over flange base 34A and lie adjacent, with this exemplary ostomy faceplate, upon outer tape portion 32. It can be seen that upper portion 41 of pouch 40 will be trapped between guard 10 and outer tape portion 32 of faceplate 30 providing several advantages to the wearer. One advantage is that intestinal gas is restricted and thus ballooning of upper portion 41 of the pouch is avoided. Another advantage is that guard 10 preferably entraps the pouch when positioned as illustrated relieving pressure on the seal of the faceplate 30 to the body as pouch 40 fills and becomes heavier.

This embodiment is particularly suited to nighttime use because of its larger dome size. The dome provides substantial advantages heretofore not readily apparent. The structure allows the wearer to confidently sleep, change positions and even roll over on the guard without fear of compromising the integrity of the pouch and/or faceplate seal to the body.

Figure 7:
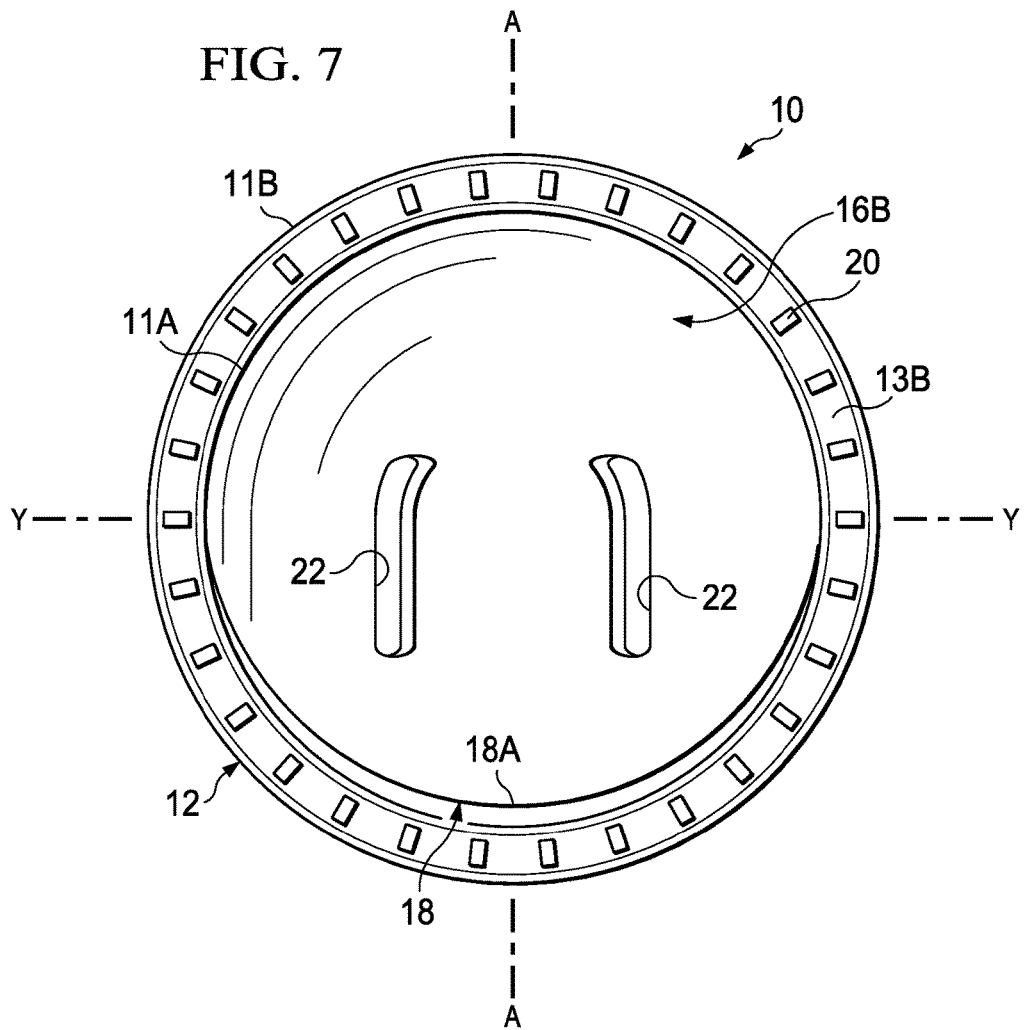
FIG. 7 is a rear view of the ostomy guard of FIG. 1 illustrating an alternative annular base ring configuration.

Now referring to FIG. 7, annular base ring's back side 13B is shown with optional periodic guard protrusions 20 which create discontinuous contact that facilitates blood flow in the non-contact areas. This embodiment is best utilized with large flange sizes close to the size of the annular inner circumference 11A, whereby guard 10 will be positioned adjacent the engaged coupling members of the faceplate and pouch as is explained in further detail below.

In view of the fact that there are many commercially available flange sizes, it becomes advantageous to supply an assortment of adapter sizes for use in conjunction with a guard, allowing a guard to be supplied in one universal diameter. For example, if the diameter of an annular base ring on a guard is three and a half inches in diameter, and a flange base in combination with hydrocolloid adhesive member of the faceplate flanges are less than two and a half inches in diameter, then the pressure applied by a guard to a faceplate may cause engaged flanges to bulge or protrude into the body of a guard. This could impede flow to some extent, especially if a guard is less domed and more streamlined.

Figure 8:
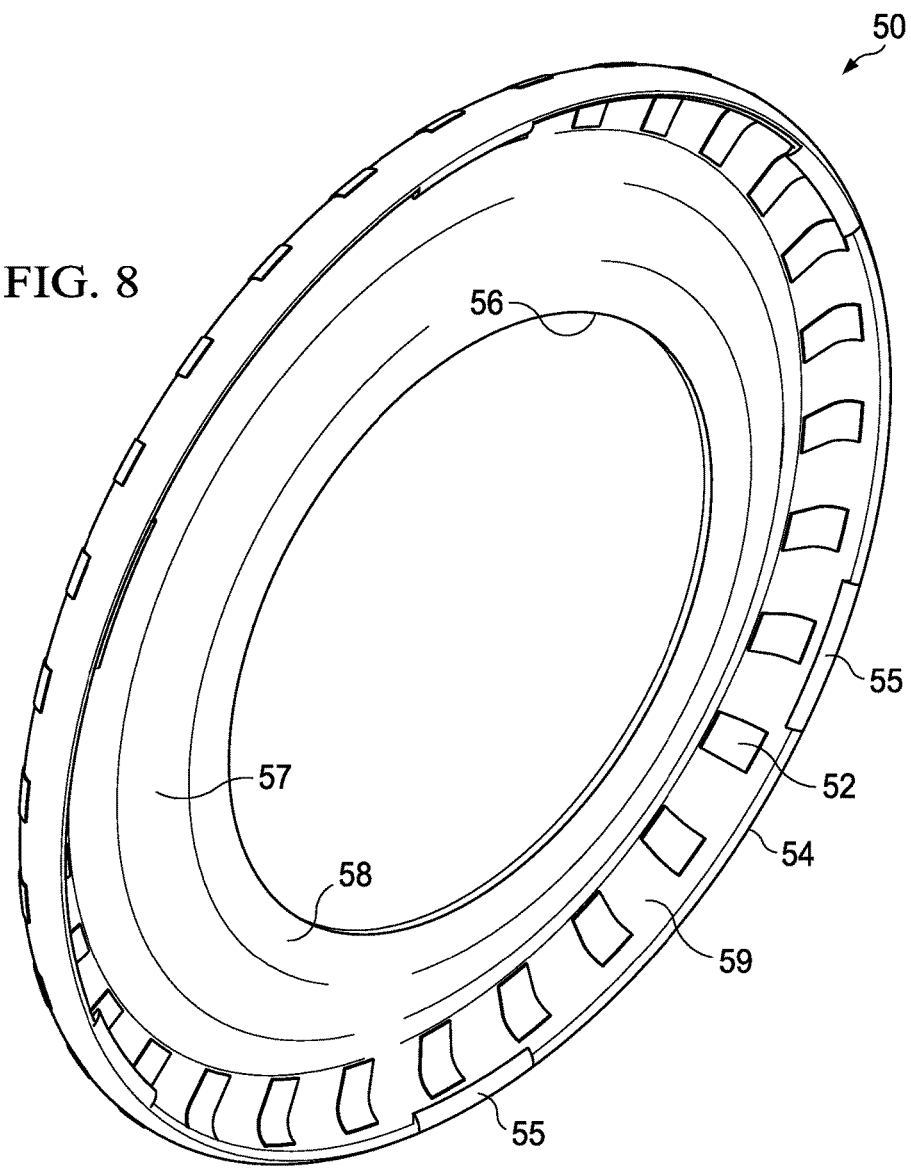
FIG. 8 is a front perspective view of an adapter for an ostomy guard.

FIG. 8 is a perspective view of one embodiment of an adapter 50. The size of the adapter's centrally located aperture 56 is selected by user so that flange base sizes smaller than the diameter of the annular base ring 12 of the guard 10 are restrained by integral support wall 58 of adapter 50, from protruding into the body 14 of the guard 10. Adapter 50 defines a centrally located aperture 56, a sloping section 57 between integral support wall 58 and a guard-receiving channel 59, and a lip 54 extending from the edge of said guard-receiving channel. The angle of sloping section 57 may be varied, however, from that shown. The angle can vary from 0 to 90 degrees (i.e., up to about perpendicular with integral support wall 58). In this embodiment, the adapter lip 54 further comprises integral retaining ribs 55. The lip 54 should allow one to snap on and maintain placement of said guard 10. It is most preferred that lip 54 extend radially inwardly to better engage with guard 10. Integral retaining ribs 55 contact annular base ring 12 of guard 10 in use, which provide a mechanical interlock and assist in retaining annular base ring 12 in guard-receiving channel 59. In another embodiment, annular base ring 12 of the guard 10 may comprise the integral retaining ribs 55 allowing for the same mechanical interlock or "snap-on" effect. Centrally located aperture 56 has a diameter that encircles the engaged coupling members 34B and 42 of the user's preferred appliance, enabling a guard to maintain its position proximate a stoma. The diameter of centrally located aperture 56 is selected so that, in use, a space or flange clearance area will be defined between the pouch flange 42 and the centrally located aperture 56. This flange clearance area allows for ease of placement and removal of the adapter 50 and allows for use of the invention without interference to the secure coupling of pouch flange 42 and coupling member 34B. It is desirable to allow for a flange clearance area of approximately ⅛ inch (about 0.32 centimeters), although the width of the flange clearance area may vary as long as the desired function is provided. About centrally located aperture 56, the adapter 50 may be provided with a rolled or flat edge. A rolled edge may be preferable when the adapter is worn adjacent to a heat weld between a pouch and a faceplate of a one-piece pouching system to maintain integrity of the pouch. A flat edge may be preferable when the adapter is worn adjacent a pouch flange 42 of a two-piece system so that it may lie flat against the pouch flange. Pouch tabs prevent integral support wall 58 from getting between flange base 34A and pouch flange 42 when coupling members 34B and 42 are coupled. However, a user may prefer to remove pouch tabs 44A, 44B, and 46 (or a given manufacturer may not provide such pouch tabs). Reasons for removal may be because pouch tabs may extend too far and insert themselves between the outer tape and faceplate side of guard receiving channel 59, causing discomfort and/or itchiness. It is advantageous to provide a thicker integral wall so that said integral support wall 58 cannot inadvertently wedge between flange base 34A and pouch flange 42. A thickness of at least about 1/16 inch (0.16 cm) has been found to be suitable, but this may be varied to provide the optimal thickness. Optional adapter protrusions 52 create discontinuous contact facilitating blood flow in the non-contact areas. Itchiness or tingling, which may be caused by pressure on the skin, may also be relieved by the presence of such adapter protrusions. The integral support wall 58 can be a continuous flat surface or comprise a plurality of discontinuous flat surfaces in a planar configuration, thus allowing for intermittent points of contact between said integral support wall 58 and faceplate 30. A discontinuous configuration will allow for greater blood flow between the areas of contact.

Adapter 50 may be formed of any suitable material that can be suitably formed into the desired configurations as explained above and exemplified in the figures. Adapter 50 may be flexible or non-flexible or a combination thereof. Non flexible materials that may be used were described supra in reference to suitable guard materials. The adapter may advantageously be more flexible than the guard for increased comfort to the user. Accordingly, more flexible materials may be used such as thermoplastic elastomers (TPE) or thermoplastic vulcanizates (TPV) and their blends. However a degree of rigidity is needed so that the adapter restrains the engaged coupling members of an appliance from protruding into the cavity of the guard body in use. A plurality of apertures (not shown) may be defined in place of the adapter protrusions 52 extending outwardly from the adapter 50 as illustrated in FIG. 8. A flexible material may be overlaid, in the guard-receiving channel 59, for example in the form of a gasket. The flexible material extends through the apertures and thus forms flexible protrusions which make resilient contact with the user's appliance. Lip 54 may also be made of flexible material that may facilitate disengagement of the adapter from the guard. Flexible materials may be removable, as in the case of a gasket or insert, or permanently adhered to the guard by bonding in overmoulding and co-injection processes. The adapter may alternatively be formed of similar polymer material as the coupling member of the ostomy faceplate and pouch flanges. Heavy texture, a pattern, or possibly lettering provided in relief on the faceplate side of an adapter 50 stamped or molded inside the groove 59 may facilitate blood flow in the non-contact areas when constant pressure is applied from form fitted clothing or a security strap 24. The relief pattern or lettering can also serve as assembly indicia to ensure the device is properly installed.

Figure 8A:
FIG. 8A is a cross sectional view of the adapter of FIG. 8 along its diameter.
Figure 11:
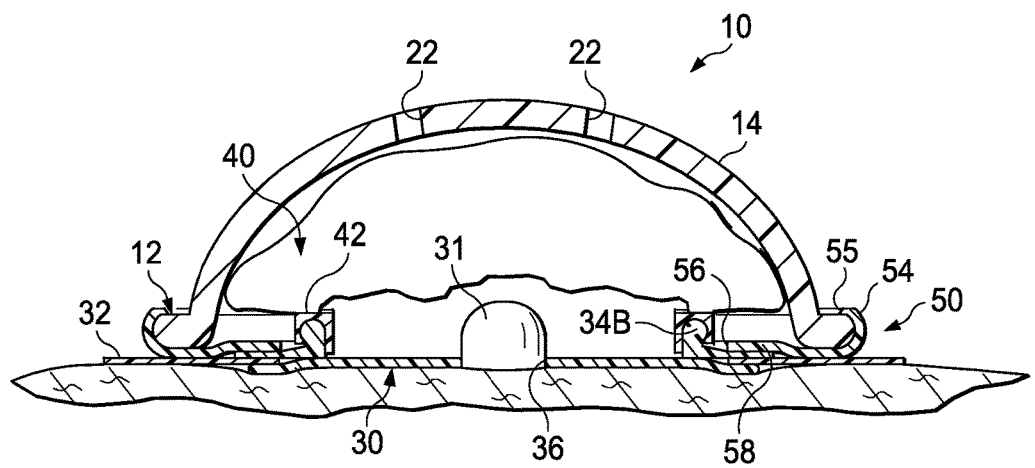
FIG. 11 is a cross sectional view of the ostomy guard of FIG. 3 in use in combination with the adapter along Y-Y.

FIG. 8A is a cross-section of adapter 50 along its diameter, illustrating integral retaining ribs 55 and together, with said guard-receiving channel 59 form a mechanical interlock with annular base ring 12 of guard 10 as shown in FIG. 11. The adapter's ability to 'snap on' is especially useful in that the guard 10 remains in position until the user decides to remove it. The adapter 50 may be selectively removed at the discretion of the user who may employ a grasping means (tab, indenture, ribbed protrusion or the like) on the exterior surface of the adapter lip 54 or body 14 of guard 10 to assist in removing the guard from the adapter.

Now referring to FIG. 9, the placement of adapter 50 on a faceplate 30 is illustrated to exemplify placement and clearances. Adapter 50 has a faceplate side which lies adjacent to the faceplate 30 when in use and a pouch side that lies adjacent the pouch 40 when in use. The pouch side of adapter will also engage the guard 10 when secured together. Although a user can apply the adapter before engaging appliance flanges, it is also possible, and may be more convenient for a particular user, to apply it after appliance flanges are engaged, as will be described below. Integral support wall 58 may further provide an adhesive means on the faceplate side adapted to attach adapter 50 to the flange base 34A to keep it from moving or rotating. FIG. 9A is a cross section of a faceplate 30 along the direction of line B-B of FIG. 9 utilizing a convex faceplate 30. FIG. 9B is a cross section along line B-B utilizing a level faceplate 30. As can be seen, sloping section 57 can be varied and distance x can be varied depending on the type of faceplate employed by the user.

FIG. 9A reflects a typical convex faceplate 30. Flange base 34A is in contact with integral support wall 58 of adapter 50. The sloping section 57 is more angled to maintain, but not add to, the convexity already applied by the exemplary faceplate 30. Additional convexity may be achieved through use of commercially available faceplates fit with shallow, medium or deep convexity, inserts, paste, gaskets or wafers. The more pronounced slope may be more suitable for an ostomate who needs convexity, and who has a short, flush or recessed stoma. When annular base ring 12 of guard 10 (not shown) is snapped into guard-receiving channel 59 of adapter 50, pressure (i.e., via form fitted clothing or a security strap) is applied to flange base 34A by support wall 58, thus aiding the stabilization of the peristomal region, and insuring the stoma will protrude as intended, thereby facilitating output of waste more readily into a pouch.

FIG. 9B reflects a typical level faceplate 30. The sloping section 57 of the adapter 50 is less pronounced than when compared with the faceplate 30 in FIG. 9A. The less pronounced slope 57 of FIG. 9B provides more support in the peristomal region for an ostomate who does not need the convexity illustrated in FIG. 9A. The support wall 58 of the adapter 50 provides support and may prevent such maladies as parastomal hernias that result from the lack of support. Adapter 50 may also be provided with adapter protrusions 52 extending from guard-receiving channel 59 across the support wall 58.

In case liquid output behind the faceplate causes the hydrocolloid adhesive member 38 to loosen from the skin, the hydrocolloid adhesive member 38 may push into a cavity formed by sloping section 57 and sealed by guard receiving channel 59 that provides a temporary reservoir for effluent allowing the user time to change the appliance before escape of output occurs.

Figure 10:
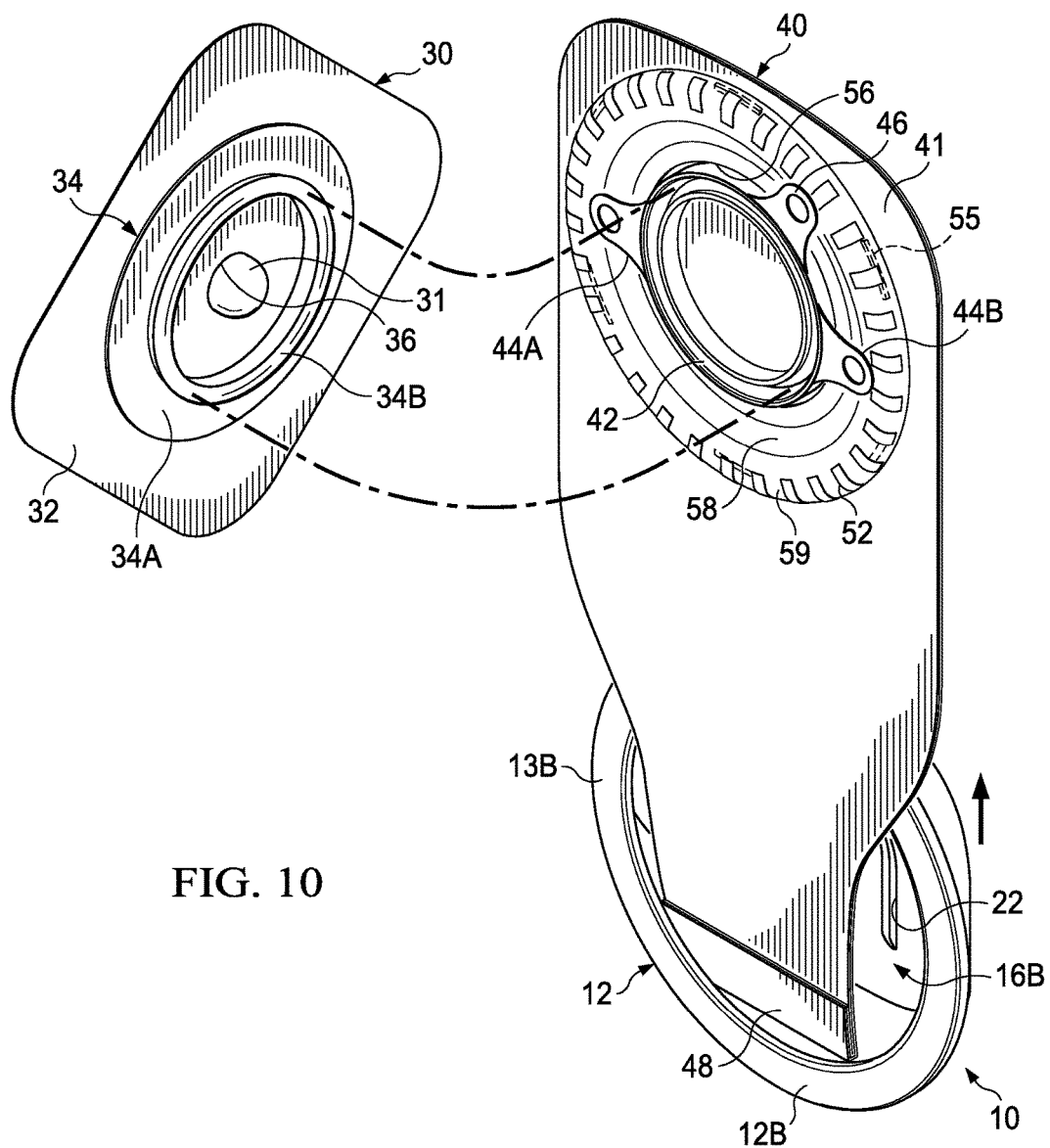
FIG. 10 illustrates placement of the adapter of FIG. 8 onto a pouching system.

FIG. 10 illustrates placement of an adapter 50 on a pouching system. Once the pouch flange 42 is engaged with coupling ring 34B, adapter 50 is applied the same way as the guard 10. The pouch end 48 is guided through the rear of centrally located aperture 56 and is lifted up and over upper portion 41 of the pouch and situated between the pouch 40 and the faceplate 30 and centrally located aperture 56 circumferentially surrounding engaged appliance flanges 42 and 34B. As previously stated, a flange clearance area is thereby created between the adapter and the engaged couplings of the user's appliance. A suitable dimension for the flange clearance area is ⅛ inch (0.3175 cm). The user can apply and remove the adapter with relative ease without having to disengage pouch flange 42 from coupling member 34B. Commercial tabs 44A, 44B, and 46 are sometimes removed from the pouch 40 for greater comfort as discussed above. Guard 10 is shown in position to be applied by guiding pouch end 48 in through rear central aperture 16B of guard 10, then out through front aperture 16A. The arrow in FIG. 10 indicate that guard 10 is then lifted upwards until body 14 of guard 10 encompasses the now engaged flanges, (i.e., coupling member 34B and pouch flange 42), and annular base ring 12 is engaged with adapter 50.

FIG. 11 shows a cross-section of the system of the invention as properly engaged on a user, along the line Y-Y of FIG. 3 (except that in FIG. 3, only guard 10 is shown). FIG. 11 illustrates the annular base ring 12 of FIG. 1 is received into guard-receiving channel 59 of adapter 50 and retaining ribs 55 contact said annular base ring 12 and assist in maintaining it in the desired engagement. Lip 54 is shown extending radially inwardly, which also assists in maintaining annular base ring 12 in position as described above.

Figure 12:
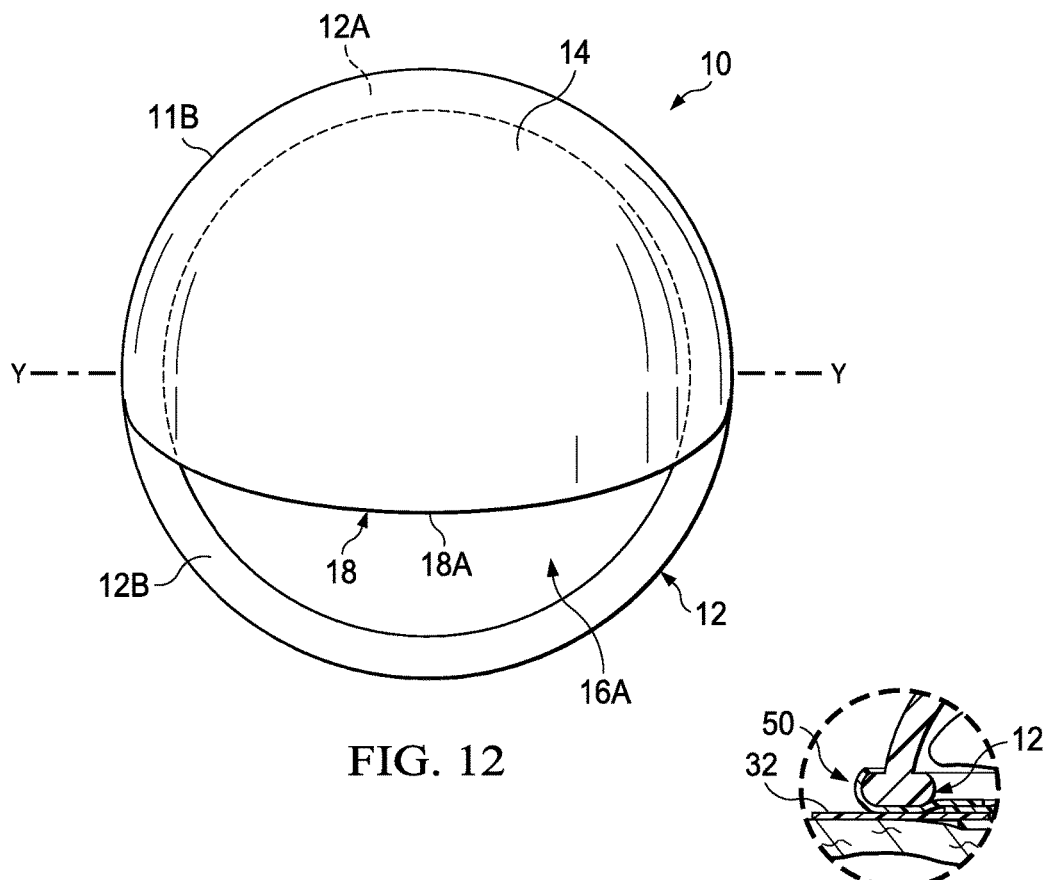
FIG. 12 is a front view of an ostomy guard with a variation of the body of the guard.

FIG. 12 illustrates another variation of a guard 10 wherein parabolic edge 18 as shown in FIG. 1 has been altered so that it is now more flattened edge 18 and body 14 is partially oblate (elliptical). This design provides a more sleek profile for the user. First portion 12A of annular base ring 12 is longer in this variation due to differences in the intersection of body 14 with annular base ring 12.

Figure 12A:
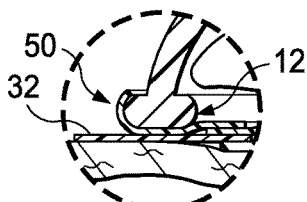
FIG. 12A is a partial cross sectional view of an alternative configuration of the annular ring in use in combination with the adapter along Y-Y of FIG. 12.

FIG. 12A illustrates a variation of FIG. 12 in which the inner circumference 11A and outer circumference 11B are essentially equidistant from where body 14 intersects annular base ring 12. This allows engagement of the guard 10 with an adapter 50 and equalization or concentration of pressure centralized to the guard-receiving channel 59 and said channel 59 of the adapter 50 can be shaped to closely engage the flared annular base ring 12.

Figure 13:
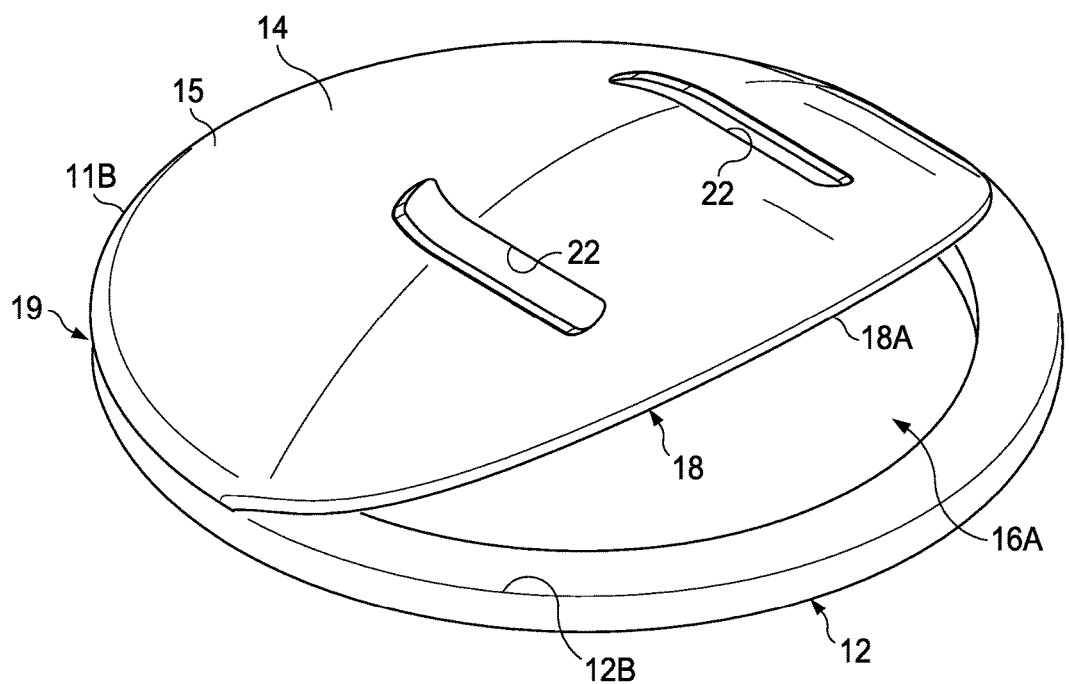
FIG. 13 is a front perspective view of an ostomy guard with a variation of the body and annular ring of the guard.
Figure 14:
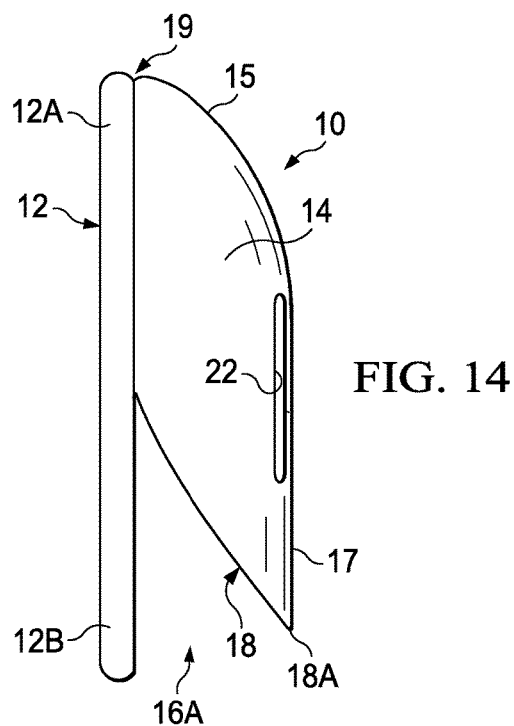
FIG. 14 is a side view of the ostomy guard of FIG. 13.
Figure 15:
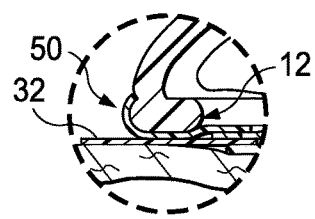
FIG. 15 is a partial cross-sectional view of the ostomy guard of FIG. 13 in use in combination with the adapter along Y-Y.

FIG. 13 illustrates another variation of an ostomy guard 10 with several alternative features that may be employed alone or in conjunction with one another or substituted into the embodiment shown in FIG. 1. In FIGS. 13 and 14, guard 10 has an annular base ring 12 circling and integral to a substantially rigid cup shape body extending perpendicularly from the annular base ring's outer circumference 11B, instead of said annular base ring's inner circumference 11A as was illustrated in FIG. 1. The capacity of the dome may vary depending on whether the dome extends from 11A or 11B. Increased capacity may be desirable to allow more room for build-up of gas during wear, thus avoiding ballooning of the pouch above the waistline of pants or trousers in use. Manufacturing considerations, such as materials, cost and methodology may make the embodiment of FIG. 1 more preferable than the embodiment of FIG. 13 or vice-versa. Another variation is the curvature on the dome. The device illustrated in FIGS. 13 and 14 is more streamlined and sleek, which may be desirable if less bulging is desired under clothing. The curvature of the dome must still allow flow of the output from the user's stoma. Body 14 may be provided with a slight indentation 19 which engages with lip 54 of an adapter 50 as shown in FIG. 15 which is an enlarged partial cross section of the engagement area of the guard and adapter.

Figure 16:
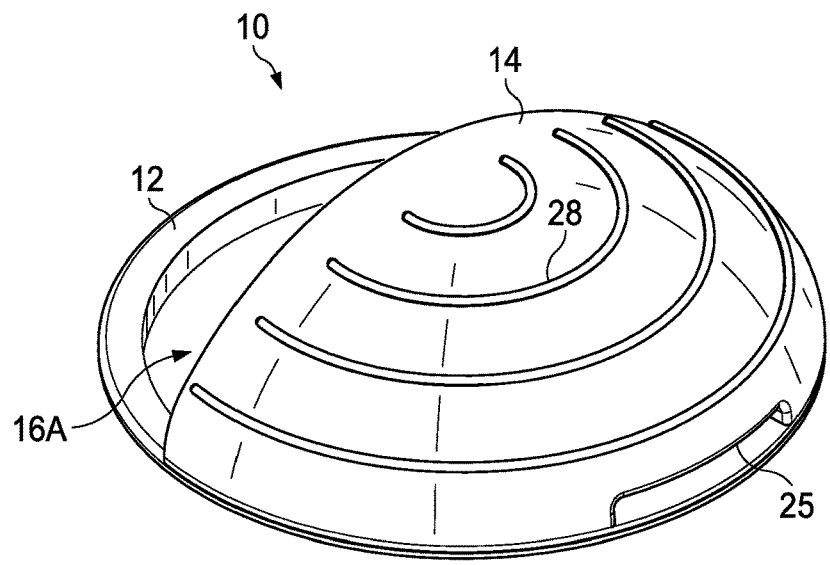
FIG. 16 is a front perspective view of an ostomy guard showing a more oblate configuration of the body.
Figure 16A:
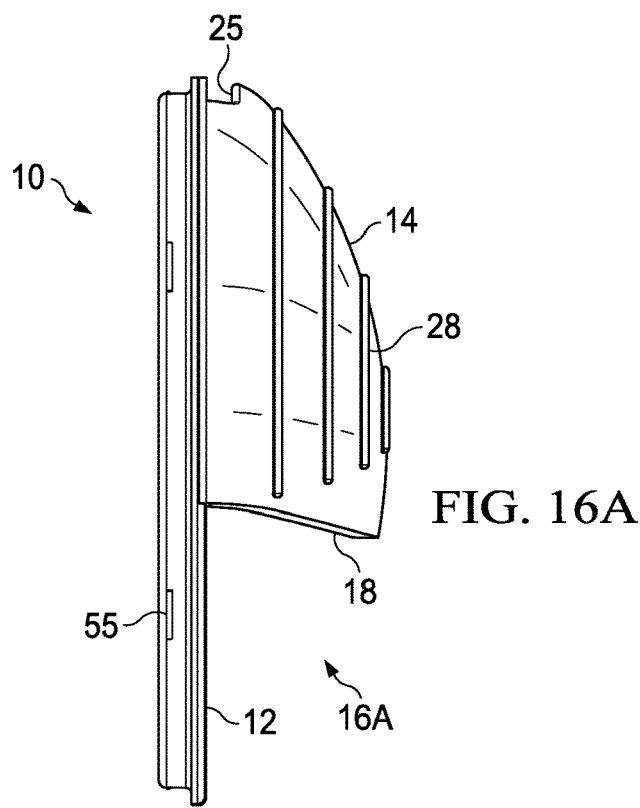
FIG. 16A is a side view of the ostomy guard of FIG. 16 showing in further detail the alternative annular ring and various other features.
Figure 17A:
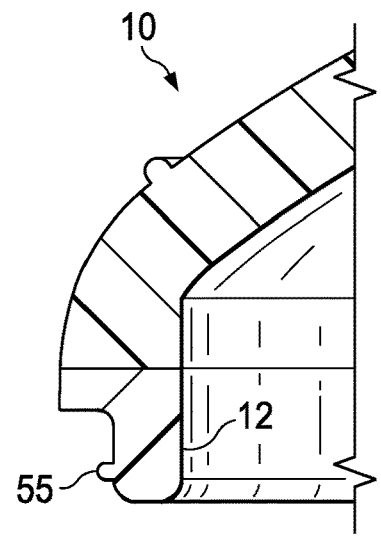
FIG. 17A is a partial cross sectional view of the alternative annular ring configuration of the ostomy guard of FIG. 16.

FIG. 16 is a perspective view of another variation of a guard 10 where body 14 extends from outer circumference 11B, but annular ring 12 defines an undercut, which is best shown in FIGS. 16A and 17A. The thickness of the guard's annular ring 12 is increased to impart greater strength and to accommodate an alternate means to attach an adapter. In this example, retaining ribs 55 are provided on the annular ring 12 instead of on the adapter 50. A flattened edge 18 (as in FIG. 12) is employed in this embodiment. Optional texture 28, here shown in the form of semi-circular protrusions on the outside of body 14, functions to prevent form-fitted clothing (e.g., a waistband) from sliding up and down on the front of the guard 10 in use. Other shapes, words or patterns may be employed instead of the illustrated semi-circular protrusions. A vent/finger niche 25 is optimally provided for ventilation and may assist a user with separating guard 10 from adapter 50 during disassembly.

Figure 17B:
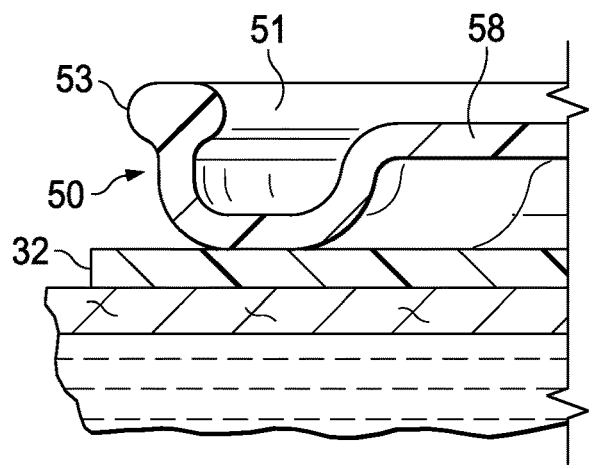
FIG. 17B is a partial cross sectional view of an alternative adapter for an ostomy guard of FIG. 16.

FIG. 17A is a partial cross sectional view showing the undercut configuration of the annular ring 12 integrally attached to body 14, and also showing one example of the configuration of the retaining ribs 55. Other configurations of attachment means may be contemplated including possibly a complete ring around the lower portion of the undercut annular ring 12 or retaining ribs 55 angled in opposite configuration from what is seen in this example with the bottom flat side turned up. FIG. 17B is preferred adapter for use with the ostomy guard variation shown in FIGS. 16 and 16A wherein a rolled edge 53 is provided on the adapter's outer side of lip 54 as a means to grip and displace the adapter 50 from the guard 10 in use. Also, an inner rolled edge 51 on the inner side of lip 54 of the adapter 50 may be utilized to complete the mechanical 'snap on' feature of this preferred guard system.

Figure 18:
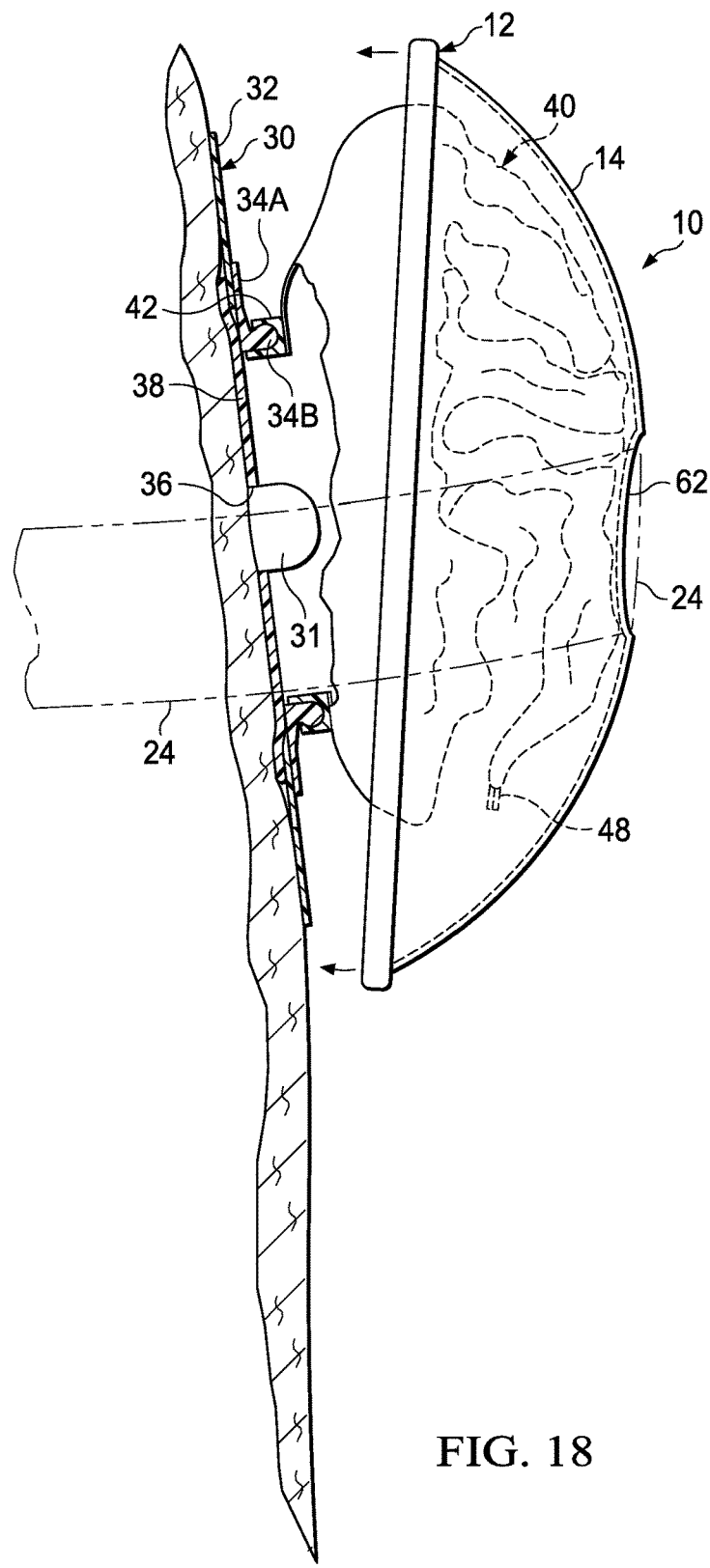
FIG. 18 is a side view of an ostomy guard that completely encloses a faceplate and pouch.

FIG. 18 illustrates another variation of an ostomy guard 10 having an annular base ring 12 comprising a sealing layer or overlay coextensive with annular base ring 12. Annular base ring 12 is applied directly against the skin of the user encompassing the entire appliance of the user as worn. Pouch 40 can be rolled or folded to fit inside guard 10. This variation may be used as a temporary guard while the user is showering or for other short-term circumstances. No apertures are provided in body 14 in order to keep fluids from entering the interior thereof. Depression 62 is shown located on the front of the body 14 and could be varied by extending it in a lateral direction along the Y-Y axis. Depression 62 is adapted to receive security strap 24 as a means to attach and maintain placement directly on the skin of the wearer, completely enclosing a pouching system that is adhesively attached to a wearer. The body 14 or annular ring 12 may be formed with any suitable material that provides flexibility and conformity to varied body shapes and to provide a sealing means. A sponge-like material may also be applied along the inner circumference 11A of annular base ring 12 to absorb any leaks that may pass through the outer sealing means. This variation on the guard is symmetrical along the A-A and Y-Y axes.

Figure 19:
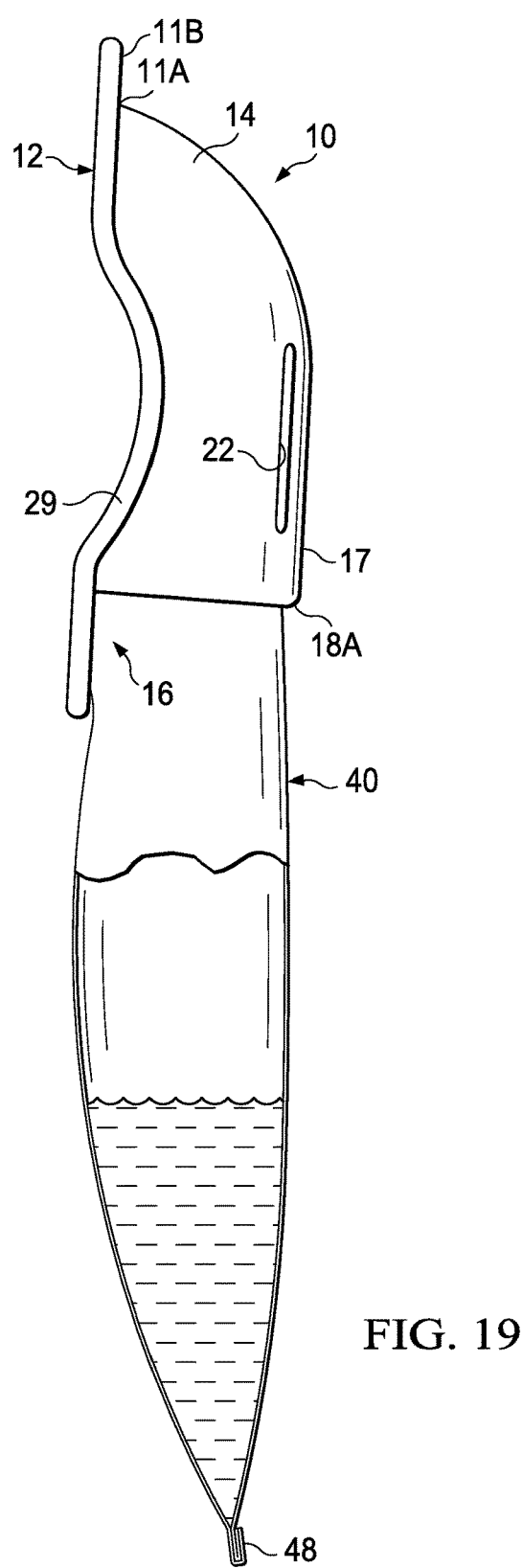
FIG. 19 is a side view of an ostomy guard with a variation in the body and annular ring of the guard.

FIG. 19 illustrates another variation of an ostomy guard 10 with an annular base ring 12 that is molded to accommodate a roll of fat that a user may have in the area of the stoma. As shown, bridge 29 provides a curvature that lies adjacent the stoma and allows for the roll of fat of the user. Alternatively, bridge 29 may extend out towards the apexes of first portion 12A and second portion 12B. When extended completely, bridge 29 would become annular base ring 12.

I claim:

1. A guard system for use with an ostomy appliance having a faceplate and a waste-collection bag for receiving waste from a user's stoma, said guard system comprising a guard adapted to protect the stoma and the adhesion of an ostomy appliance faceplate, said guard comprising:
   a substantially rigid domed body, integral to which is an annular base ring having an inner circumference and an outer circumference, said annular base ring having a bottom portion and a top portion joined to the domed body;
   a rear aperture defined by the inner circumference of the annular base ring;
   a front aperture defined between the bottom portion of the annular base ring and the domed body for accommodating a waste-collection bag extending into the rear aperture and out through the front aperture to hang over the bottom portion of said annular base ring;
   the annular base ring applies pressure around the entire circumference of a taped portion of the faceplate for reducing loss of adhesion during use; and,
   the domed body further comprising a securing strap and positioning said securing strap to cause, when said securing strap is wrapped around a user to hold the guard system against a user's body, the guard system to apply even pressure around the circumference of the annular base ring against the taped portion of the faceplate.

2. The guard system of claim 1, wherein said guard's domed body has an inner surface and an outer surface, and wherein the inner surface contacts the waste-collection bag when the waste-collection bag is inserted through said rear and front apertures.

3. The guard of claim 1, wherein said securing strap is a belt.

4. The guard system of claim 1, wherein an inner circumference of the domed body aligns with said inner circumference of said annular base ring, and annular base ring extends partially beyond an outer circumference of said domed body.

5. The guard system of claim 1, wherein an outer circumference of the domed body aligns with the outer circumference of the annular base ring and the annular base ring extends inwardly beyond an inner circumference of the domed body wherein it joins the annular base ring.

6. The guard system of claim 1, wherein said annular base ring has a predetermined width sufficient to mitigate discomfort to said user and further comprises an edging secured to said outer circumference.

7. The guard system of claim 1, wherein said top portion of said annular base ring is pressed against and trapping an upper portion of the waste-collection bag, and bottom portion of said annular base ring is pressed directly against the faceplate of said ostomy appliance.

8. The guard system of claim 1, further comprising an adjustable belt so that, when the adjustable belt is placed around the user during use of the guard system, said annular base ring of the guard is pressed against the faceplate of the user's ostomy appliance and an upper portion of said waste-collection bag is tucked into the domed body.

9. The guard system of claim 1, further comprising an adapter for placement between the annular ring of the guard and the faceplate of the user's ostomy appliance; said adapter comprising an integral sloping section on a support wall defining a centrally located adapter aperture and a guard-receiving channel for receiving said guard's annular base ring, the centrally located aperture configured to completely encircle an external surface of a flange of the waste-collection bag.

10. The guard system of claim 9, wherein, said centrally located adapter aperture has a diameter greater than that of the flange, enabling said guard to maintain its position encircling the flange of the waste collection bag.

11. The guard system of claim 9, wherein said adapter further comprises protrusions extending from said guard-receiving channel for contacting the faceplate of the user's ostomy appliance.

12. The guard system of claim 9, wherein said sloping section on said support wall has a slope sufficient to form a temporary reservoir to indirectly retain escaping effluent underneath the faceplate, and effluent is sealed under the faceplate by pressure applied to the outer taped portion of the faceplate by said guard system's guard receiving channel located on an outer circumference of said adapter, allowing a user time to change the ostomy appliance before experiencing a sudden loss of output.

13. A method of protecting a stoma and the adhesion of an ostomy appliance faceplate using an ostomy guard, comprising:
   guiding a waste-collection bag of an ostomy appliance, in through a rear aperture of said ostomy guard then out through a front aperture of said ostomy guard;
   lifting said ostomy guard until a domed body surrounds an upper portion of the waste-collection bag, including one or more flanges or weld connections of said ostomy appliance, and in the process trapping a portion of said waste-collection bag between an annular base ring and a taped portion of said ostomy appliance faceplate; and,
   applying pressure derived from either a securing strap and/or one or more form fitted articles of clothing to said ostomy guard's domed body, thereby transmitting an even application of pressure by the annular base ring against the taped portion of the faceplate.

14. The method of claim 13 further comprising using an ostomy appliance adapter by snapping the annular base ring of the ostomy guard into an adapter's guard receiving channel in a mechanical interlock and applying pressure derived from either a securing strap and/or form fitted articles of clothing to said ostomy guard's domed body for an even application of pressure by the annular base ring with said attached adapter against the taped portion of the ostomy appliance faceplate.

15. A guard system for use with an ostomy appliance having a faceplate and a waste-collection bag for receiving waste from a user's stoma, said guard system comprising a guard adapted to protect said user's stoma and the adhesion of an ostomy appliance faceplate, said guard comprising:
   a substantially rigid domed body and an integral annular base ring having an inner circumference and an outer circumference, said annular base ring having a bottom portion and a top portion joined to the domed body;

a rear aperture defined by the inner circumference of the annular base ring; and, an adapter comprising an integral support wall having a faceplate side and a waste-collection bag side, and further defining a centrally located aperture, wherein said guard's annular base ring is received into said guard's receiving channel; and said centrally located aperture configured to completely encircle an external surface of an ostomy appliance waste-collection bag flange or weld connection and, the annular base ring applies pressure around the entire circumference of a taped portion of the faceplate for reducing loss of adhesion during use.

16. The guard system of claim 15 wherein said domed body is adapted with one or more depressions to help retain a security strap.

17. The guard system of claim 15, wherein said domed body further comprises a securing strap and positioning said securing strap to cause, when the securing strap is wrapped around a user to hold the guard system against an user's body, the guard system to apply even pressure around the circumference of the annular base ring against to the taped portion of the faceplate.

18. The guard system of claim 15, wherein the adapter comprises a sloping section on said support wall and a guard-receiving channel located on the outer circumference of said sloping section on said support wall defining an outer edge of said adapter, and a lip extending from an edge of said guard-receiving channel, and wherein said guard's annular base ring is received into said guard's receiving channel in a mechanical interlock.

19. The guard system of claim 15, wherein the domed body has two axes of symmetry and does not have a front aperture.

20. The guard system of claim 15, wherein one or more additional sealing layers are coextensive with the outer circumference of the adapter.

* * * * *